US00PP31282P2

(12) United States Plant Patent
Hansen

(10) Patent No.: US PP31,282 P2
(45) Date of Patent: Dec. 24, 2019

(54) ***KNIPHOFIA* PLANT NAMED 'FLASHPOINT'**

(50) Latin Name: *Kniphofia hybrida*
Varietal Denomination: Flashpoint

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 24 days.

(21) Appl. No.: 16/350,526

(22) Filed: Nov. 28, 2018

(51) Int. Cl.
*A01H 5/02* (2018.01)

(52) U.S. Cl.
USPC ..... Plt./443

(58) Field of Classification Search
USPC ..... Plt./443
See application file for complete search history.

*Primary Examiner* — Annette H Para

(57) ABSTRACT

A new and distinct cultivar of Red Hot Poker plant named *Kniphofia* 'Flashpoint' with long, gracefully-arching, strap-like, keeled, glaucous, gray-green foliage and numerous scapes beginning in mid-summer and repeating though early fall. Habit is densely-growing, winter-hardy and tolerant of heat. Numerous scapes with dense flowers of intense chartreuse-yellow buds and creamy flowers. The new plant is useful for landscaping as a specimen, en masse, or as a long-lasting cut flower.

1 Drawing Sheet

Botanical classification: *Kniphofia hybrida.*
Variety denomination: 'Flashpoint'.

STATEMENT REGARDING PRIOR DISCLOSURES UNDER 37 CFR 1.77(b)(6)

The first public disclosure of the claimed plant, in the form of a sale, was made by Walters Gardens, Inc. on May 14, 2018. Prior to that, on Dec. 1, 2017 the claimed plant was displayed with a photograph and brief sales promotion on the website of Walters Gardens, Inc., who obtained the plant and all information relating thereto, from the inventor. No plants of *Kniphofia* 'Flashpoint' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to the new and distinct Red Hot Poker, *Kniphofia* 'Flashpoint' developed under the direction of the inventor at a wholesale perennial nursery in Zeeland, Mich., USA in the summer of 2013. The new plant was the result of a single seedling selection from a cross of 'Papaya Popsicle' U.S. Plant Pat. No. 22,915 as the female or seed parent and 'Percy's Pride' (not patented) as the male or pollen parent in Aug. 22, 2013. The plant passed initial evaluation in the summer of 2015 and was subsequently given the breeder code 13-8-21 prior to naming. *Kniphofia* 'Flashpoint' has been successfully asexually propagated by division method since 2015 at the same wholesale perennial nursery in Zeeland, Mich. and subsequently by shoot tip tissue culture, and both methods have been found to be stable and produce identical plants that maintain the unique characteristics of the original plant through successive generations.

SUMMARY OF THE PLANT

*Kniphofia* 'Flashpoint' differs from its parents as well as all other *Kniphofia* known to the applicant. The most similar known *Kniphofia* cultivars are the female parent 'Papaya Popsicle', 'Solar Flare' U.S. Plant patent application Ser. No. 16/350,525 and 'Pineapple Popsicle' U.S. Plant Pat. No. 22,969. 'Papaya Popsicle' is much shorter in scape and foliage height with more yellow-orange flower coloration. 'Pineapple Popsicle' is smaller in scape height, foliage height and overall habit and has a deeper yellow flower buds and fewer flowers per inflorescence. 'Solar Flare is slightly shorter in scape and foliage and the flower is more yellowish, and the flowers begin earlier in the summer. 'Percy's Pride' is taller with more light-yellow to lime-colored flowers and the flower heads are larger. 'Sally's Comet' has a deeper yellow flower with smaller flower heads.

*Kniphofia* 'Flashpoint' differs from these above cultivars and all cultivars known to the inventor in that it has:

1. Gracefully arching, strap-like, keeled, gray-green foliage.
2. Rapidly growing, dense habit, winter-hardy, heat tolerant, rabbit and deer tolerant, moderate-sized clumps.
3. Numerous spikes of chartreuse-yellow buds that mature to a cream-color on medium height stems;
4. Flowering beginning mid-summer and repeating into early October in Michigan.

BRIEF DESCRIPTION OF THE DRAWINGS

The photographs of *Kniphofia* 'Flashpoint' demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
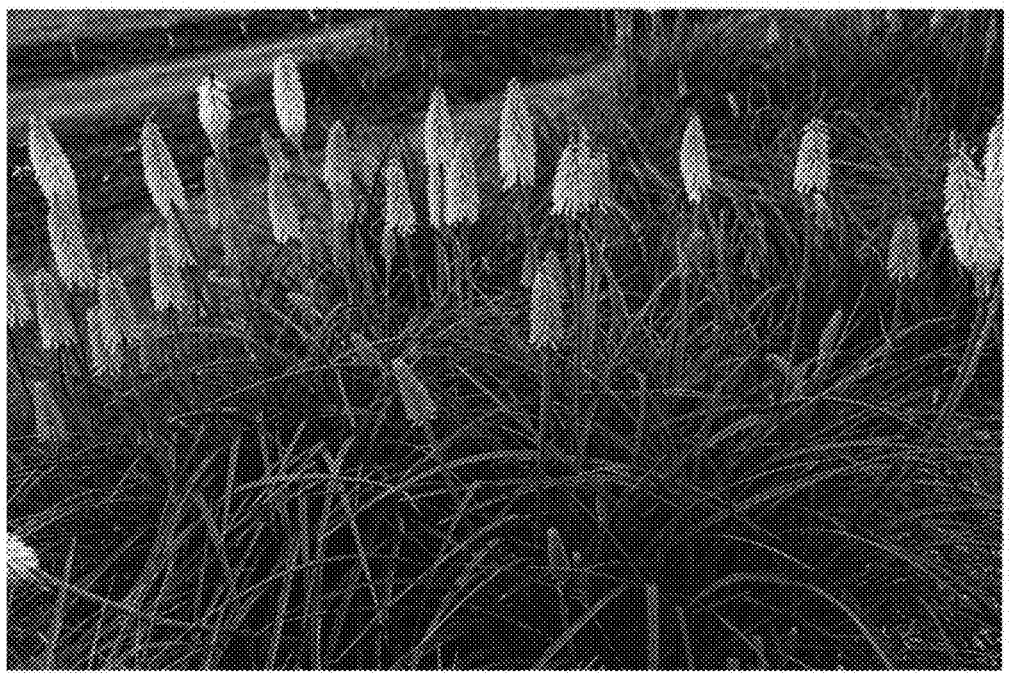
FIG. 1 shows the side-view habit of a five-year-old plant in midseason flowering.
Figure 2:
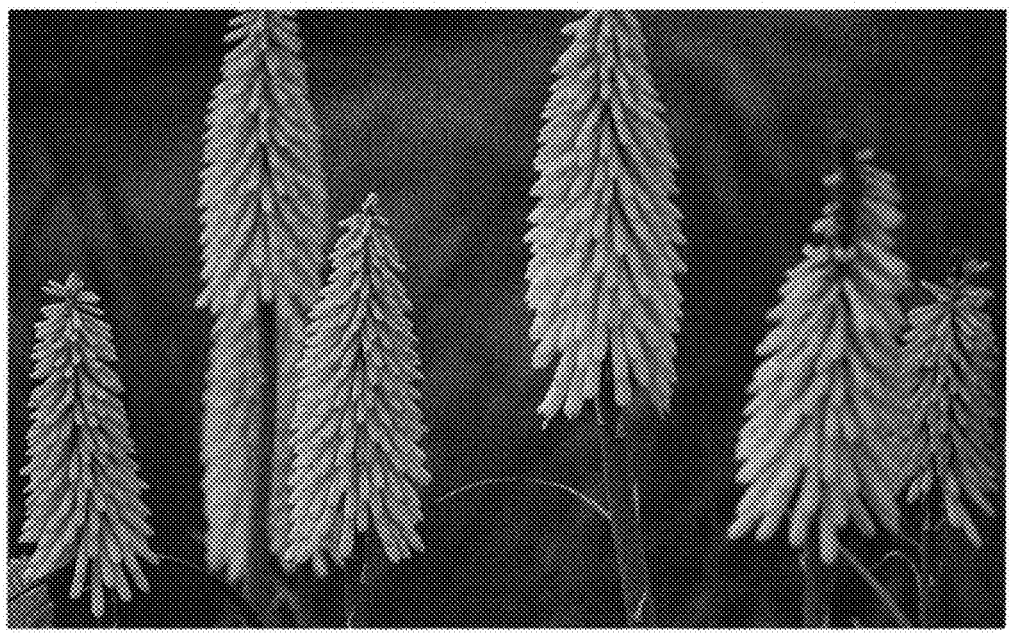
FIG. 2 shows a close-up of the flowers and buds.

The following descriptions and color references are based on the 2015 edition of The Royal Horticultural Society Colour Chart except where common dictionary terms are used. The new plant, *Kniphofia* 'Flashpoint', has not been observed under all possible environments. The phenotype may vary slightly with different environmental conditions, such as temperature, light, fertility, moisture and maturity levels, but without any change in the genotype. The following observations and size descriptions are of a five-year-old plant in a trial garden of a wholesale perennial nursery in Zeeland, Mich. under full sun with supplemental water and fertilizer as needed.

Botanical classification: *Kniphofia* hybrid;

Parentage: *Kniphofia* 'Papaya Popsicle' as the female or seed parent and 'Percy's Pride' as the male or pollen parent;

Propagation method: By garden division of the rhizome and shoot tip tissue culture;

Growth rate: Vigorous, flowering in 3.5 liter containers in about 10 to 12 weeks from a 25 mm plug liner in late winter to spring and from a one-year-old bare root plant to flowering in 6 to 8 weeks in a 4.0 liter container;

Rooting habit: Fibrous from base of rhizomes, lightly branching; color nearest RHS 158C;

Plant description: Dense, rhizomatous, acaulescent, perennial clump with long thin foliage to about 146.0 cm across and about 70.0 cm tall; flowering to about 98.0 cm tall; about 46 peduncles per plant;

Leaves: Linear; keeled at base, triangular in distal half; arranged about 8 leaves per basal division; apex narrowly acute; base truncate, clasping; margin entire; no fragrance observed;

Leaf size: To about 112.0 cm long and 25.0 mm across at base, average about 92.0 cm long and 18.0 mm across at base;

Leaf color: Young base nearest RHS 150D both abaxial and adaxial, distally nearest RHS 144A and RHS 138A both abaxial and adaxial; mature adaxial and abaxial nearest RHS 138A;

Leaf venation: Parallel; color same as leaf abaxial and adaxial;

Stem: Acaulescent; rhizome about 20.0 mm across at base;

Inflorescence: In spike-like raceme; cylindrical; about 200 flowers per stem; flowering portion to about 37.0 cm tall and about 6.0 cm across; lasting about three weeks; flower spacing less than 1.0 mm apart on raceme in distal region and about 2.5 cm in lowest flowers;

Peduncle: Cylindrical; glabrous; glaucous; solid not fistulose; to about 98.0 cm long and 12.0 mm diameter; average 74.0 cm tall and 10.0 mm diameter;

Peduncle color: Nearest RHS 146C;

Buds one day prior to opening: Oblong-ellipsoidal to tubular with swollen subacute apex and rounded base; glabrous; lustrous; about 27.0 mm long and about 2.5 mm diameter at base and 6.0 mm diameter at widest point near apex;

Bud attitude: Beginning outwardly and drooping as maturing toward anthesis;

Bud color: Abaxial distal and dorsal portions one and five days prior to opening nearest RHS 4D with midrib nearest RHS 4C;

Flowers: Cylindrical forming tubular corolla; perfect; actinomorphic; individually open and effective about three to four days;

Flower size: To about 36.0 mm long to tip of exserted, fused in basal about 25.0 mm; face to about 10.0 mm tall and about 9.0 mm wide; corolla tube about 3.5 mm diameter near base and about 5.5 mm near throat; corolla tube to 28.0 mm long;

Flower attitude: Drooping;

Flower fragrance: None detected;

Flowering period: Individual racemes effective for about 3 weeks; beginning mid-summer Michigan for about six week, then continuing with repeat racemes until early fall with a short two-week break in the heat of the summer;

Tepals: Six, in two sets of three; both sets with acute apices and fused in basal 25.0 mm forming tube; margin entire; glabrous and lustrous abaxial and adaxial; about 28.0 mm long and about 3.0 mm across just above fusion point;

Tepal color (young abaxial): Both outer and inner sets nearest RHS NN155A at anthesis with midrib or nearest RHS 1D; (young adaxial): both tepal sets between RHS NN155A and RHS 4D;

Tepal color (mature abaxial): Both inner and outer sets identical with midribs nearest RHS 1D and remainder nearest RHS NN155A; (mature adaxial): inner and outer sets identical nearest RHS NN155A;

Androecium: Six; variable lengths;

*Filaments*.—Six; exserted; cylindrical; glabrous; lustrous; from about 28.0 to 34.0 mm long and about 0.7 mm diameter; color nearest RHS 155B.

*Anther*.—Slightly flattened ellipsoidal; dorsifixed; longitudinal; flattened ventrally to dorsally; about 2.0 mm long and 1.5 mm across and 1.0 mm thick; color nearest RHS 14B.

*Pollen*.—Abundant: color nearest RHS 11A.

Gynoecium: Single; about 30.0 mm long;

*Style*.—Cylindrical; glabrous; lustrous; about 26.0 mm long and 0.7 mm diameter: color nearest RHS 2D.

*Stigma*.—Flattened, round; about 0.3 mm across; color nearest RHS 158B.

*Ovary*.—Superior; dome-shaped; rounded apex, truncate base; about 3.0 mm long and 2.0 mm diameter; color nearest RHS 144A.

Pedicel: Cylindrical; glabrous; stiff; drooping with maturity; about 3.0 mm long and about 1.0 mm diameter;

Pedicel color: Nearest RHS 144A;

Bracts: Lanceolate; at cauline nodes and subtending individual flowers; with acute apices and truncate base; to about 7.0 mm long and 4.5 mm across at base; decreasing distally; average about 6.0 mm long and 3.5 mm across; color nearest RHS 158D;

Fruit: Tri-valved loculicidal capsule; globose to ellipsoidal; about 7.0 mm long and 5.0 mm across; glabrous; with rounded apex and rounded base; typically four to nine seeded; color upon maturity nearest RHS 199A;

Seed: Irregular with angular sides, acute apex and base; about 5.0 mm and 3.0 mm across; color nearest RHS 200A;

Disease and pest resistance: 'Flashpoint' resistance beyond that of other *Kniphofia* has not been observed. The plant grows best with good drainage and is able to tolerate some heat when established. Hardiness at least from USDA zone 6 through 9 and 5b with protection.

I claim:

1. A new and distinct cultivar of *Kniphofia* plant named 'Flashpoint' as herein described and illustrated.

* * * * *